United States Patent [19]

Wong

[11] Patent Number: 5,227,304
[45] Date of Patent: Jul. 13, 1993

[54] METHOD FOR COUNTING WHOLE BLOOD DILUENT AND DETERGENT REAGENT SYSTEM

[75] Inventor: Show-Chu Wong, Sunnyvale, Calif.

[73] Assignee: Sequoia Turner Corporation, Mt. View, Calif.

[21] Appl. No.: 918,162

[22] Filed: Jul. 21, 1992

Related U.S. Application Data

[63] Continuation of Ser. No. 641,975, Jan. 16, 1991, abandoned.

[51] Int. Cl.$^5$ .................. G01N 31/00; C11D 3/48
[52] U.S. Cl. .................................. 436/17; 436/18; 436/179; 252/106
[58] Field of Search .................. 436/10, 17, 18, 179; 252/106

[56] References Cited

U.S. PATENT DOCUMENTS 4,962,038 10/1990 Carter et al. .................. 436/10
5,008,202 4/1991 Edmondson et al. .................. 436/18

*Primary Examiner*—John W. Rollins
*Attorney, Agent, or Firm*—Richard D. Schmidt

[57] ABSTRACT

An improved multi-purpose blood diluent for use with a gentle lysing agent and improved detergent reagent system are disclosed which are especially suitable for use in routine electronic enumeration and volumetric differentation of blood cells. The preferred imidazole stabilizer used in the diluent reagent is found to be an excellent cell stabilizing agent and buffer for maintaining cell morphology during operation. A synergistic combination of a superior antimicrobial agent, the preferred Triadine-10, used in the diluent and the detergent reagents, not only prevents bacterial or fungal growth, but also helps to stabilize cells and to obtain distinct volumetric differentiation of certain leukocyte subpopulations. The preferred Brij 35 in a balanced salt solution has proved to be an efficient and cost effective detergent to ensure accurate results and trouble-free operation of the analyzers.

13 Claims, No Drawings

METHOD FOR COUNTING WHOLE BLOOD DILUENT AND DETERGENT REAGENT SYSTEM

This application is a continuation of application Ser. No. 07/641,975, filed Jan. 16, 1991, now abandoned.

BACKGROUND OF THE INVENTION

1. Field of the Invention

This invention concerns methods for counting blood, blood diluents, antimicrobial agents, and detergent reagent systems especially suitable for use in enumeration and sizing of blood cells, including white blood cell subpopulations.

2. Description of the Prior Art

Analytical data of blood are important as an index of health and well being. The analysis of blood cell populations provides useful information for diagnosis and treatment, since they show a rapid response to variations in medical condition.

Most analytical methods rely on the fundamental cell property of volume regulation. Each type of cell in the circulating blood has its own characteristic volume, ranging from as small as 2 cubic microns for platelets to over 450 cubic microns for polymorphonuclear cells. Automated, blood-analysis instruments have been developed to accomplish the measurement of blood cells and related components with simplicity and rapidity. Such measurements include white blood cell count (WBC), red blood cell count (RBC), platelet count (PLT), hematocrit (HCT), hemoglobin (HGB), the mean corpuscular volume (MCH), and the mean corpuscular hemoglobin concentration (MCHC), as well as WBC subpopulations such as lymphocytes, monocytes, and granulocytes.

Before making blood cell counts by means of an automated, blood-analysis instrument, the blood is diluted to a certain concentration. The diluent comprises a stable and balanced water solution of chemical salts providing an electrolytic solution capable of conducting current to which a blood sample can be added so as to dilute the red blood cells, white blood cells, platelets and other blood components and enable the desired parameters of these blood components to be measured, counted and evaluated, see, for example, U.S. Pat. Nos. 4,213,876; 4,244,837; 4,521,518; 4,745,071; 4,485,175; 4,286,963; and 4,617,275.

In analyzing blood by an automated, blood-analysis instrument or other analytical method (including manual microscopic evaluations), it is essential that the diluent not adversely affect the chemical and physical integrity of the blood cells during the analysis. For instance, if the blood diluent is not isotonic and osmotically balanced with respect to the blood, the blood cells may shrink or expand. Importantly, the diluent should not adversely affect the blood analysis itself.

The diluent must also be free from particles which may interfere with the analysis of the blood. While the diluent is normally filtered to remove particles larger than 0.2 micron in diameter at the time of its manufacture, the diluent may be susceptible to the support of microorganism growth after the manufacture and packaging of the diluent. The presence of microorganisms may result in inaccurate and non-reproducible results.

It is a common practice to include an antimicrobial agent in blood diluents to retard the growth of microorganisms. The antimicrobial agent, as with other components of the diluent, must not adversely affect the blood cells or adversely affect or interfere with the analyses. Thus, while antimicrobial agents in blood diluents are desirable, caution must be observed in their selection and use.

An antimicrobial agent which has been employed for many years in blood diluents is sodium azide. Its use has not, however, been without significant problems. First, the presence of sodium azide has been found to influence the formation of cyanmethemoglobin, a chromogen formed for determining hemoglobin in a blood sample. For instance, without sodium azide in the diluent, the hemoglobin as determined photometrically may be significantly different than that with the azide present. Second, aqueous solutions of sodium azide are highly toxic (toxicity level of 6 on a scale of 1 to 6). See Gosselin et al. (eds.), Clinical Toxicology of Commercial Products, The Williams and Wilkins Company, Baltimore, 5th Edition, 1984, (Section IID, position 111). Finally, the disposal of sodium azide through copper or lead-containing plumbing systems may result in the formation of heavy metal azides which may increase over extended periods of time.

Despite the need for alternatives to sodium azide as an antimicrobial agent in blood diluents, few alternatives have been proposed. An attempt has been made to substitute other preservatives for sodium azide and an example of this is shown in U.S. Pat. Nos. 3,692,125 and 4,102,810 where 2-phenoxyethanol is used as an antimicrobial agent.

There are disadvantages to the use of phenoxyethanol as well. First, phenoxyethanol is a rather weak antimicrobial agent. It has been found to be more effective when used in conjunction with other preservatives, such as the hydroxybenzoates. Martindale, The Extra Pharmacopoeia (27th edition, The Pharmaceutical Press, London, 1977, page 1281). Second, while less toxic than sodium azide, phenoxyethanol is still toxic (toxicity level of 4 on a scale of 1 to 6). See Gosselin et al., supra (Section IID, position 463). Most importantly, phenoxyethanol can affect red cell MCV/hematocrits and white cell differentiation with each type of blood analyzer. Finally, in U.S. Pat. Nos. 3,962,125 and 4,102,810, sodium fluoride is essentially included along with phenoxyethanol in the proposed diluent to enhance hemoglobin chromogen formation. Sodium fluoride is only slightly less toxic that sodium azide (toxicity level of 4–5). See Gosselin et al., supra (Section IID, position 100).

A further attempt to substitute other preservatives for sodium azide can be found in U.S. Pat. No. 4,238,634, in which sodium dehydroacetate is used as an antimicrobial agent. Sodium dehydroacetate, a fungicide, is toxic at high doses but is less toxic than sodium azide, sodium fluoride, and phenoxyethanol (toxicity level of 3). See Gosselin et al., supra (Section IID, position 1187).

EDTA as a preservative is disclosed in U.S. Pat. No. 5,008,262 filed on Nov. 29, 1988. This case is also assigned to the assignee hereof. Japanese publication CA 95(25): 21726j discloses that the effectiveness of preservatives for reagents in clinical analysis was studied in the Heart Infusion Liquid Medium and the SYB medium. Among others, sodium omadine and Triadine-10 were found useful.

The diluents, cleaners, detergents and other reagents of the prior art, while useful, have not been completely satisfactory.

Accordingly, it is an object of the present invention to substantially overcome one or more problems of the art.

Another object is to provide a diluent and a detergent that do not interfere with the blood analysis.

Objects and advantages other than those set forth will be apparent from the following description.

In many automatic blood analyzers, such as the Cell Dyn ® 2000 analyzer, separate baths are used for dilution of aliquot samples of blood. The operation of the Cell Dyn 2000 is fully described in the Operation Reference Manual for Cell Dyn 2000CS Hematology Analyzer (1989), available from Unipath Corporation, Mountain View, California (Sequoia-Turner Corporation).

The inventive diluents, reagents, cleansers and the like, although they may be employed with other hematology analyzers, are particularly suitable with the Cell Dyn 2000 analyzer. The following description is given with this analyzer in mind, although the steps may easily be extrapolated to other analyzers.

Typical analyzers including the Cell Dyn 2000 employ a set of internal dilution baths, one for white cells and one for red cells and platelets, which hold the prepared dilutions during each measurement cycle. Each bath contains a transducer with a specific size orifice embedded in it. During each measurement cycle, the orifice senses and initially sizes each diluted cell drawn through it. Volumetric metering ensures that a precise amount of diluted specimen is measured during each cycle. System self-cleaning occurs automatically, after each measurement.

The diluent mentioned above is the "diluent" of this invention and the self-cleaning is done with the "detergent" of this invention. The effectiveness of the detergent can be judged by the analyzer maintaining a low "count time" and a substantially trouble free performance.

During every cycle, whole blood (150 or 250 microliters) is aspirated directly into a specimen (shear) valve which isolates two precise amounts of blood and dilutes each non-serially. During this process, 0.8 microliters of whole blood is isolated and dispensed into the Red Blood Cell/Platelet (RBC/PCT) dilution bath by the action of an RBC syringe. This 1:12,500 ratio RBC/PLT dilution is used to measure the number and size of the red cells (erythrocytes) and platelets (thrombocytes).

Simultaneously, 32 microliters of whole blood is isolated and dispensed into the White Blood Cell (WBC) dilution bath by the action of the WBC dispense syringe. During transport, this 1:250 ratio WBC/HGB (hemoglobin) dilution is mixed with a lytic agent (lysate) that changes the membrane of each cell, causing cytoplasm and hemoglobin to rapidly release from each red cell leaving a membrane that is less than 2 femtoliters. The lytic action compresses each white cell membrane, causing the cytoplasm to diffuse slowly from it as the membrane shrinks around the nucleus and, when present, cytoplasmic granules. This lysate affected dilution is used to measure the number and modified size of the white cells (leukocytes). Following the white cell measurement cycle, the remaining lysed 1:250 dilution is transported to the hemoglobin flow cell where the amount of released hemoglobin is measured.

Cell detection occurs in an orifice sensing zone. As each cell is drawn into a constant current, flowing from an external electrode through the orifice sensing zone to an internal electrode, a change in electrical conductivity occurs generating an equivalent voltage pulse. The number of pulses generated during each measurement cycle corresponds to the number of cells sensed. Whereas, the amplitude of each pulse is directly proportional to the volume of the cell is represents (initial sizing).

Electronic sizing to differentially classify the lysate modified white cells is possible only when specially formulated reagents are used. These reagents control the release of cytoplasm from the white cells. When specimens having a "normal" leukocyte differential are electronically sized in this manner, the three or five white cell sub-populations are obtained.

A typical analyzer will employ from about 100 to 300 microliters of whole blood and will determine the cell analysis in a dilute volume containing various reagents. Typically WBC/HGB (1:250) One part whole blood in a total volume of 250 parts "diluent" and lyse and RBC/PLT (1:12500) One part whole blood in a total volume of 12500 parts diluent.

A typical analyzer will employ some combination of the following procedure:

aspirate the whole blood isolate the aspirated blood in a shear valve: 32 microliters for WBC/HGB dilution and 0.8 microliters for RBC/PLT dilution activate the RBC "diluent" dispense syringe to transport the aspirated blood (0.8 $\mu$L) to the RBC/PLT transducer bath (1:12500 ratio)

activate the WBC "diluent" dispense syringe to transport the aspirated blood (32 $\mu$L) to the WBC transducer bath (1:250 ratio)

activate the lyse dispense syringe to add a specific volume of lyse to the dilution as it enters WBC bath mix both dilutions obtain a zero reference for the HGB measurement count and size the cells present in both dilutions transport the WBC dilution to the HGB flow cell and optically measure the amount of hemoglobin present rinse each transducer bath and orifice, and metering tubes and the HGB flow cell—with a "detergent"

analyze the data display and print the results.

Reagents must meet specific criteria to maintain the cell volume (size) for each cell measured during size data collection—cell volume should not be altered by diluent. Resistance methodology sizes and counts cells based on detection of a change in resistivity during measurement. Poor performance can result from slight differences in resistivity between the diluent and detergent used or between reagents currently in use and those used when electronic calibration was set.

Lyse and diluent compatibility is essential to ensure that accurate sizing information is obtained for the white cells and that remaining red cells stroma are electronically eliminated.

Isotonic Diluent

Diluent is formulated for use to meet the following specifications:

Contain fewer than 400 particles per milliliter with a size of one femtoliter or greater.

Provide background count display values equal to or less than:

| RBC: 0.05 M/$\mu$L | WBC: 00.2 K/$\mu$L |
| --- | --- |

-continued

| HGB: 00.2 g/dL | PLT: 005. K/μL |

Maintain diluted cell volume of each red cell and platelet stable in the 1:12,500 dilution during count and sizing portion of measurement cycle.

Maintain, when used in conjunction with Lyse and detergent system, cell membrane integrity for each white cell during determination of the lysate modified white cells size distribution.

The diluent is an azide-free isotonic stabilizing electrolyte solution. The organic buffer together with inorganic salts and stabilizers provide an osmotically balanced solution and thus maintain pre-existing red cell volume and stabilize the leukocyte subpopulations. The diluent must also meet selected performance specifications and correlate (Normal Range) with the reagent system on the following parameters:

| WBC ± 0.2 | PLT ± 5 |
| RBC ± 0.05 | MPV ± 0.5 |
| Hgb ± 0.15 | Lymph % ± 1.5 |
| MCV ± 1.0 | Mono % ± 1.5 |
| RDW ± 0.5 | Gran % ± 1.5 |

Isotonic Detergent

Detergents are required for use in hematology analyzers, to ensure repeated accurate results by the removal of excess reagents or sample. They are also used in some analyzers in a photometric volume metering section where the formation of a stable meniscus is vital to instrument precision. Ordinary soaps and detergents are not useful in this context due to several inherent problems. First, the introduction of additional chemical components into the system provides an additional source of background noise which could potentially interfere with accurate hematological analysis. Secondly, the use of conventional soaps and detergents creates a foaming problem within the containers used to supply and store reagents, samples and "washes." The creation of a soapy foam can interfere with the proper volumetric metering of liquid reagents and sample fluids. Also, the foaming problem can trip sensors, thus interferring with normal operation, and cause containers to overflow despite apparently normal liquid levels.

The detergent of the instant invention minimizes all of the above-mentioned difficulties experienced with conventional detergents and soaps.

The Detergent is formulated for use to meet the following specifications:

Same requirements as diluent.

Provide sufficient wetting action to rapidly remove air bubbles from the entire flow system at installation and during auto-startup mode.

Drain completely from each metering tube prior to each measurement cycle.

Provide proper meniscus formation in metering tube and maintain it during each run cycle.

Rinse, with minimal bubble formation, each metering tube, flow system, inside of each transducer, and hemoglobin flow cell.

Maintain count times within acceptable limits for up to 1000 cycles by preventing accumulation of orifice debris.

Provide an optically clear solution which is required for zero reference during the hemoglobin measurement cycle.

Lyse

The Lyse, generally described in U.S. Pat. No. 4,745,071, is formulated for use to meet the following specifications:

Change and compress the white cell membrane causing it to slowly diffuse cytoplasm as it shrinks around the nucleus and, if present, cytoplasmic granules.

Change red cell membrane causing it to release hemoglobin and rapidly shrink leaving minimal stroma—less than 2 femtoliters.

Convert released hemoglobin to hemoglobin complex that is measurable within 20 seconds.

Enzymatic Cleaner

The Enzymatic Cleaner is used during the Auto-Clean cycle to effectively clean the flow system and transducers. It removes blood components and residue and reduces the background count to insignificant levels. This cleaner is described in patent application 07/641,974, filed concurrently herewith.

ISOTONIC DILUENT

The inventive isotonic diluent contains several components. A leucoprotector such as dimethyl urea may optionally be used.

Antimicrobial agents are also necessary. Preferred agents are sodium omadine and Triadene 3 or 10 mentioned above in amounts sufficient to prevent substantial microbial contamination.

Sodium omadine is sodium 2-pyridinethiol-1-oxide and Triadine-10 is a mixture of about 6% sodium omadine with about 60% hexahydro-1,3,5-tris (2-hydroxyethyl)-s-triazine. Triadine-3 is hexahydro-1,3,5-tris(2-hydroxyethyl)-s-triazine.

The diluent as well as the Detergent contains inorganic salts such as alkali metal halides or sulfates, preferably including sodium or potassium chloride, sodium fluoride and sodium or potassium sulfate in amounts appropriate to achieve isotonic balance.

The diluent will also contain a buffer. The buffer may be any organic physiological buffer. Exmaples of appropriate biological buffers are triethanolamine, imidazole, TRIS, B.E.S., HEPES, MOPS, MOPSO. Tris is tromethamine, CAS #77-86-1, 2 amino-2-hydroxymethyl-1,3-propanediol.

BES is N,N-bis(2-hydroxyethyl)-2-aminoethanesulfonic acid.

HEPES is N-(2-hydroxyethyl)piperazine-$N^1$-(2-ethanesulfonic acid).

MOPS is 3-(N-Morpholino) propanesulfonic acid.

MOPSO is 3-(N-Morpholino)-2-hydroxypropane sulfonic acid.

The preferred buffer is imidazole 1,3-diaza-2,4-cyclopentadiene. The buffer is also critical as a leucoprotector.

Ethylene diamine tetracetic acid salts (EDTA) may also be used if desired as a chelator and to enhance the antimicrobial character of the diluent.

As mentioned above, the Diluent must have good antimicrobial action and not interfere with performance. Many antimicrobials may be used, such as phenoxyethanol, chlorobutanol, phenylethanol, 4-chloroxylenol, paraben derivatives, glutaraldehyde, formaldehyde, nalidixic acid and the like. Some of the antimicrobials affect the white cell distribution and thus must be carefully checked. The preferred antimicrobials to substantially prevent contamination are Sodium Omadine—a registered trademark of the Olin Corporation; 1-hydroxy-2(1H) pyridinethione (CAS# 1121-30-8); Olin Brochure 735-015R6 eff. 3/89 and Triadine-10 (a registered trademark of the Olin Corporation); a mixture of Omadine sodium salt with 1,3,5 Triazine-1,3,5-(2H, 4H, 6H)-triethanol (CAS# 72103-18-5) Olin brochure 735-019R5 Eff. 3/89 or Triadine-3 which is just the 135 Triazine without the omadine.

The amount used of these agents will be sufficient to prevent contamination. This is usually about 0.2 to 5% of the composition but may vary outside of this range. The pH is adjusted to 6.7 to 8.2, preferably 6.9 to minimize deleterious effects. Common inorganic acids such as sulfuric, hydrochloric, phosphoric and the like as well as short chain organic acids may be used.

The formulation must be substantially isotonic. Accordingly, an osmolality of about 290+20 must be obtained by appropriate adjustment of the components.

All parts, percentages, and proportions herein and in the appended claims are by weight unless otherwise specified.

The preferred Inventive Diluent Composition is as follows:

| | Component | Amount g/l | |
|---|---|---|---|
| a. | Alkali metal chloride | 0–6 | |
| b. | Alkali metal sulfate | 0–15 | (10–16 Total a, b, c) |
| c. | Alkali metal fluoride | 0–2 | |
| d. | Imidazole | 0.2–5 | |
| e. | Dimethylurea | 0–5 | |
| f. | EDTA | 0–2 | |
| g. | Sodium Omadine | 0.05–5 | |
| h. | Triadine-10, Triadine-3 | 00.5–5 | (0.1–5 Total g & h) |
| i. | pH adjusting agent | 6.2–8.2 pH | |
| j. | Water balance | | |

ISOTONIC DETERGENT

The Isotonic Detergent composition as mentioned above must be compatible with the other components of the Reagent system. The inventive detergent system, accordingly, contains inorganic salts such as alkali metal halides or sulfates, preferably including sodium or potassium chloride, sodium or potassium sulfate and sodium fluoride in amounts appropriate to achieve an isotonic balance.

A surfactant will also be required, preferably a nonionic surfactant with a HLB of about 12–18. Suitable surfactants are Brij 35 Ex ICI Americas Inc. (HLB 16.9); polyoxyethylene 23 lauryl ether; Diazopon, Ex GAF, a polyoxyethylated alkylphenol; Triton X-100 Ex Rohm and Haas; Tween 20 Ex ICI Americas Inc., a polyoxyethylene (20) sorbitan monolaurate. The preferred surfactant is Brij 35.

The preferred Isotonic Inventive Detergent Composition is as follows:

| | Component | Amount g/l | |
|---|---|---|---|
| a. | Alkali metal chloride | 0–15 | |
| b. | Alkali metal sulfate | 0–15 | (10–16 a, b, c) |
| c. | Alkali metal fluoride | 0–2 | |
| d. | Dimethylurea | 0–5 | |
| e. | Triadine-10 or Triadine-3 | 0.05–5 | |
| f. | Surfactant | 1–20 | |
| | Water | Balance | |
| | pH adjusting agent | | 6–10.5 pH |

Example 1 - Diluent

| Component Formulation | A | B | C | D | E | F | G | H | I | J | K | L | M | N |
|---|---|---|---|---|---|---|---|---|---|---|---|---|---|---|
| Imidazole | 0.5 | 0.5 | 0.5 | 0.5 | 0.5 | 0.5 | 0.5 | 0.5 | .46 | .46 | 0.5 | 0.5 | 0.5 | .45 |
| Dimethyl urea | 1.0 | 1.0 | 1.0 | 1.0 | 1.0 | 1.0 | — | — | — | — | — | — | — | — |
| Sodium sulfate | 10.0 | 10.0 | 10.0 | 10.0 | 10.0 | 10.0 | 10.0 | 10.0 | 9.5 | 9.0 | 10.0 | 10.0 | 10.0 | 10.0 |
| Sodium chloride | 3.6 | 0.6 | 3.6 | 0.6 | 3.6 | 4.2 | 4.0 | 4.2 | 4.2 | 4.2 | 4.0 | 4.0 | 4.0 | 4.0 |
| Sodium fluoride | 0.2 | 0.2 | — | 0.5 | 0.5 | — | 0.2 | 0.2 | — | — | 0.2 | 0.2 | — | 0.2 |
| Potassium chloride | | | | | | | | | | | | | | |
| Sodium omadine (40%) | 0.5 | 0.5 | 0.5 | — | 0.5 | — | — | 0.3 | 0.2 | 0.2 | 0.05 | 0.3 | 0.3 | |
| Triadine-10 | — | — | — | 0.3 | — | 0.3 | 0.3 | 0.5 | 0.5 | 0.5 | 0.5 | 0.3 | — | 0.3 |
| EDTA (4Na) | — | — | — | — | — | — | 0.2 | 0.2 | — | — | 0.2 | 0.2 | 0.2 | — |
| EDTA (2Na) | | | | | | | | | | | | | | |
| EDTA (2K) | | | | | | | | | | | | | | |
| Glutaraldehyde | | | | | | | | | | | | | | 0.4 |
| pH (adjusted) | 6.9 | 6.9 | 7.0 | 6.9 | 6.9 | 6.9 | 6.9 | 6.9 | 6.9 | 6.9 | 6.9 | 6.9 | 6.9 | 6.9 |
| Osmolality (mOSm/kg) | 310 | 328 | 303 | 328 | | 324 | 307 | 318 | 306 | 299 | — | 316 | 302 | 311 |
| Conductivity (mMHO/Cm) | 17.8 | 18.7 | 17.6 | | | 18.4 | | | 18.3 | 17.9 | | | | |

| Component Formulation | O | P | Q | R | S | T | U | V | W | X | Y | Z |
|---|---|---|---|---|---|---|---|---|---|---|---|---|
| Imidazole | .45 | .45 | .45 | .46 | .46 | 0.5 | 0.46 | 0.46 | 0.46 | 0.46 | 0.46 | 0.46 |
| Dimethyl urea | — | — | — | — | — | — | — | — | 1.0 | — | — | 1.0 |
| Sodium sulfate | 10.0 | 10.0 | 10.0 | 6.0 | 9.5 | 10.0 | 10.0 | 10.0 | 10.0 | 10.0 | 10.0 | 10.0 |
| Sodium chloride | 4.0 | 4.0 | 4.0 | 4.2 | 4.2 | 4.2 | 4.2 | 4.2 | 4.2 | 4.2 | 4.2 | 4.2 |
| Sodium | 0.2 | 0.2 | 0.2 | | | | | | | | | |

-continued

Example I - Diluent

| | | | | | | | | | | | |
|---|---|---|---|---|---|---|---|---|---|---|---|
| fluoride | | | | | | | | | | | |
| Potassium chloride | | | | | | | | | | 0.3 | 0.5 |
| Sodium omadine | | 0.1 | 0.2 | 0.2 | | | 0.2 | 0.2 | 0.2 | 0.2 | 0.2 |
| Triadine-10 | 0.3 | 0.3 | 0.3 | 0.5 | 0.5 | 0.5 | 0.5 | 0.5 | 0.5 | 0.5 | 0.5 |
| EDTA (4Na) | — | — | — | | | 0.2 | | | | | |
| EDTA (2Na) | 0.2 | | | | | | | | | | |
| EDTA (2K) | | 0.2 | | | | | | | | | |
| Glutaraldehyde | | | | | | | | | | | |
| pH (adjusted) | 6.9 | 6.9 | 6.9 | 6.9 | 6.9 | 6.9 | 6.9 | 6.9 | 6.9 | 6.9 | 6.9 |
| Osmolality (mOSm/kg) | 310 | 311 | 313 | 251 | 305 | 318 | 311 | | | 312 | |
| Conductivity (mMHO/Cm) | | | 14.9 | 18.3 | 18.8 | | | | | 18.8 | |

Example II
Detergent

| Component | Concentration g/l | | | | | | | | |
|---|---|---|---|---|---|---|---|---|---|
| | A' | B' | C' | D' | E' | F' | G' | H' | J' |
| Sodium sulfate | 10.5 | 11.0 | 1.75 | 10.0 | 10.0 | 10.0 | 10.0 | 10.8 | 10.0 |
| Sodium chloride | 4.2 | 4.2 | 9.0 | 4.2 | 4.4 | 4.4 | 4.2 | 4.2 | 3.6 |
| Sodium fluoride | | | | 0.3 | 0.1 | 0.1 | 0.2 | — | 0.1 |
| Triadine-10 | 0.3 | 0.3 | 0.4 | 0.3 | | | | 0.3 | |
| Sodium Omadine (40%) | | | | | 0.04 | 0.25 | 0.3 | — | 0.25 |
| Brij 35 (30%) | 5.0 | 5.0 | 5.0 | 5.0 | 6.0 | 6.0 | 5.0 | 5.0 | 6.0 |
| pH | 10.2 | 10.2 | 9.8 | 10.2 | 5.8 | 6.0 | 5.3 | 10.5 | 6.0 |
| Osmolality (mOsm/Kg) | 306 | 315 | 316 | 306 | 306 | 306 | 305 | 312 | 283 |
| Conductivity (mMHO/Cm) | 18.4 | 18.9 | 17.4 | | 18.6 | 18.6 | 18.4 | 18.9 | 17.4 |

The compositions of Example I and II, when used in a hematology analyzer, produce acceptable results.

While certain representative embodiments and details have been shown for the purpose of illustrating the invention, various changes and modifications can be made therein without departing from the scope of the invention as defined in the appended claims.

What is claimed is:

1. A reagent system for use in an automatic hematology analyzer, wherein said reagent system comprises an isotonic blood diluent and an isotonic detergent,
said isotonic blood diluent comprising an imidazole organic buffer, an antimicrobial agent, inorganic salts and a pH adjusting agent, and
said isotonic detergent comprising inorganic salts, a surfactant, and said antimicrobial agent.

2. A reagent system of claim 1 wherein said imidazole is present at a concentration of approximately 0.2-5.0 g/l.

3. A reagent system of claim 1 wherein said antimicrobial agent is hexahydro-1,3,5-tri(2-hydroxyethyl)-s-triazine.

4. A reagent system of claim 3 wherein said blood diluent and said detergent further comprise a second antimicrobial agent, wherein said second antimicrobial agent is sodium 2-pyridinethiol-1-oxide.

5. A reagent system of claim 1 wherein said isotonic blood diluent has the following formula:

| | Component | Amount g/l |
|---|---|---|
| a. | Alkali metal chloride | 0–6 |
| b. | Alkali metal sulfate | 0–15 |
| c. | Alkali metal fluoride | 0–2 |
| d. | Imidazole | 0.2–5 |
| e. | Dimethylurea | 0–5 |
| f. | EDTA | 0–2 |
| g. | Sodium Omadine | 0.05–5 |
| h. | Triadine-10 or Triadine-3 | 0.05–5 |
| i. | pH adjusting agent | to pH 6.2–8.2 |
| j. | Water | Balance to 100% | wherein a+b+c total 10–16, and wherein g+h total 0.1–5.

6. A reagent system of claim 1 or 5 wherein said isotonic detergent has the following formula:

| | Component | Amount g/l |
|---|---|---|
| a. | Alkali metal chloride | 0–15 |
| b. | Alkali metal sulfate | 0–15 |
| c. | Alkali metal fluoride | 0–2 |
| d. | Dimethylurea | 0–5 |
| e. | Triadine-10 or Triadine-3 | 0.05–5 |
| f. | Surfactant | 1–20 |
| g. | pH adjusting agent | to pH 6–10.5 |
| h. | Water | Balance to 100% | wherein a+b+c total 10–16.

7. A reagent system of claim 6, wherein said surfactant is polyoxyethylene 23 lauryl ether and is present in a concentration of approximately 1–20 g/l.

8. A method for analyzing blood samples to electronically enumerate blood cells and volumetrically differentiate leukocyte subpopulations, wherein said method comprises the steps of:

(a) supplying a whole blood sample which is divided into a white cell aliquot and a red cell aliquot, a volume of isotonic blood diluent comprising cell stabilizing imidazole buffer, an antimicrobial agent, inorganic salts and a pH adjusting agent, a volume of a lyse, and a volume of an isotonic detergent solution comprising inorganic salts, a surfactant, and said antimicrobial agent to an automatic blood analyzer;

(b) contacting said white cell aliquot with said diluent and lyse within said automatic blood analyzer to enumerate the leukocytes and volumetrically differentiate the leukocyte subpopulations in said whole blood sample; and (c) contacting said red cell aliquot with said diluent within said automatic blood analyzer to enumerate the red cells and platelets.

9. A method according to claim 8 wherein numerous whole blood samples are sequentially supplied to said automatic blood analyzer, and wherein a volume of said isotonic detergent is sequentially used after each whole blood sale aliquot as a cleansing and rising agent following analysis by said automatic blood analyzer of said whole blood sample aliquots.

10. A method according to claim 8 wherein said antimicrobial agent is hexahydro-1,3,5-tris(2-hydroxyethyl)-s-triazine.

11. A method according to claim 8 wherein said isotonic blood diluent has the following formula:

|   | Component | Amount g/l |
|---|---|---|
| a. | Alkali metal chloride | 0-6 |
| b. | Alkali metal sulfate | 0-15 |
| c. | Alkali metal fluoride | 0-2 |
| d. | Imidazole | 0.2-5 |
| e. | Dimethylurea | 0-5 |
| f. | EDTA | 0-2 |
| g. | Sodium Omadine | 0.05-5 |
| h. | Triadine-10 or Triadine-3 | 0.05-5 |
| i. | pH adjusting agent | to pH 6.2-8.2 |
| j. | Water | Balance to 100% | wherein a+b+c total 10-16, and wherein g+h total 0.1-5.

12. A method according to claim 9 or 11 wherein said isotonic detergent has the following formula:

|   | Component | Amount g/l |
|---|---|---|
| a. | Alkali metal chloride | 0-15 |
| b. | Alkali metal sulfate | 0-15 |
| c. | Alkali metal fluoride | 0-2 |
| d. | Dimethylurea | 0-5 |
| e. | Triadine-10 or Triadine-3 | 0.05-5 |
| f. | Surfactant | 1-20 |
| g. | pH adjusting agent | to pH 6-10.5 |
| h. | Water | Balance to 100% | wherein a+b+c total 10-16.

13. A method according to claim 12 wherein said surfactant is polyoxyethylene 23 lauryl ether and is present at a concentration of approximately 1-20 g/l.

* * * * *